US006278765B1

(12) United States Patent
Berliner

(10) Patent No.: US 6,278,765 B1
(45) Date of Patent: Aug. 21, 2001

(54) PROCESS FOR PRODUCING DIAGNOSTIC QUALITY X-RAY IMAGES FROM A FLUOROSCOPIC SEQUENCE

(76) Inventor: Leonard Berliner, 18 Carol Ct., Staten Island, NY (US) 10309

(*) Notice: Subject to any disclaimer, the term of this patent is extended or adjusted under 35 U.S.C. 154(b) by 0 days.

(21) Appl. No.: 09/475,230

(22) Filed: Dec. 30, 1999

(51) Int. Cl.[7] .................................................. H05G 1/60
(52) U.S. Cl. ................................... 378/98.12; 378/62
(58) Field of Search .............................. 378/98.12, 62, 378/98; 382/128, 132

(56) References Cited

U.S. PATENT DOCUMENTS

| | | | |
|---|---|---|---|
| 5,651,042 | * | 7/1997 | Dewaele ................................ 378/62 |
| 5,832,055 | * | 11/1998 | Dewaele ................................ 378/62 |
| 6,183,139 | * | 2/2001 | Solomon et al. ...................... 387/137 |
| 6,208,709 | * | 3/2001 | MeLen .................................. 378/98.2 |

* cited by examiner

Primary Examiner—Robert H. Kim
Assistant Examiner—Irakli Kiknadze
(74) Attorney, Agent, or Firm—Goldstein Law Offices P.C.

(57) ABSTRACT

A process for producing a diagnostic quality x-ray image from a fluoroscopic sequence. Initially a sequence of numerous individual fluoroscopic images are acquired. These images are stabilized to produce stabilized individual images wherein the subject is located in a consistent position within said stabilized individual images. The stabilized individual images are fractionated and summated to create a resultant image. The resultant image unexpectedly has superior quality when compared to any of the individual fluoroscopic images.

4 Claims, 2 Drawing Sheets

PROCESS FOR PRODUCING DIAGNOSTIC QUALITY X-RAY IMAGES FROM A FLUOROSCOPIC SEQUENCE

BACKGROUND OF THE INVENTION

The invention relates to a process for producing diagnostic quality x-ray images from a fluoroscopic sequence. more particularly, the invention relates to a system by which the images of a fluoroscopic sequence are combined to form an image having superior quality when compared to the individual images from the sequence.

Trraditionally, x-ray imaging has been divided into two major classifications: radiography and fluoroscopy.

Radiography generally involves the transmission of x-rays through a subject, wherein x-ray photons that are not absorbed by the subject reach a receptor and form a "shadow" of the subject. The resulting static image is typically acquired in less than one second on the receptor, which may be a film-screen combination, or a solid state detector. If properly acquired, a relatively sharp, high resolution image results which is approved for a variety of diagnostic purposes.

Fluoroscopy also involves the transmission of x-rays through a subject. However, x-ray photons that are not absorbed by the subject strike a fluorescent screen, wherein a continuous image is recorded therefrom with a television camera or digital camera. The resulting real-time sequence of images can display movement. The images are typically acquired and displayed at up to thirty frames per second. Typically the image quality of a fluoroscopic image, or a sequence of fluoroscopic images, is limited by the relatively smaller number of photons reaching the receptor during the relatively short exposure time therefor.

Mammograms are conventionally not performed using fluoroscopy since fluoroscopic images inherently lack the quality necessary for critical examination. Thus, radiography is used which requires a long exposure time. To prevent motion artifacts from motion during the exposure, the breast is compressed, resulting in severe discomfort to the woman. In addition, because of the length of exposure, effective mammography in mobile screening centers is greatly reduced—making mammograms less accessible to the poor, and woman in rural or remote locations.

Generally, radiographic quality is compromised by a number of "artifacts". Artifacts are undesirable features of an image which make using the image for diagnostic purposes more difficult. Among these are motion artifacts and quantum mottle. Motion artifacts result from movement of the patient, especially during pediatric radiography, and in theory can even result from vibration of the image acquisition equipment. Quantum mottle occurs when insufficient photons reach the receptor, and quantization occurs to flatten the image or create a mere shadow of the subject—devoid of detail. Quantum mottle is especially pervasive with fluorography, where short exposure times can rob images of crucial detail.

Other factors which influence the usefulness of an x-ray image for a particular diagnostic purpose include the interaction between different types of human tissue with the x-ray photons. In particular, x-ray photons generated with a different "kV setting" will penetrate different tissue in varying degrees. Accordingly, different kV settings will reveal different features and abnormalities in different types of tissue. However, because conventional x-rays are acquired using a single kV setting, each image is in effect a compromise of which anatomical features to emphasize.

With regard once again to fluoroscopy, several attempts have been made to increase the usefulness of fluoroscopic images. However, by there nature, these techniques are not suited for the creation of images of diagnostic quality.

One such technique, known as "image hold" attempts to improve the quality of final fluoroscopic image through the averaging of several individual frames. However, because there is no correction for motion, increasing the number of individual frames will blur an image having motion artifact.

While these units may be suitable for the particular purpose employed, or for general use, they would not be as suitable for the purposes of the present invention as disclosed hereafter.

SUMMARY OF THE INVENTION

It is an object of the invention to provide a technique for producing a diagnostic quality image from a fluoroscopic sequence. Accordingly, the individual frames from the fluoroscopic sequence are combined to create an image which has superior quality to any of the individual frames.

It is another object of the invention to provide a technique which reduces the effects of quantum mottle. Accordingly, the use of numerous frames from the fluoroscopic sequence produces the unexpected result that the subtle variations in the individual image which represent features of the subject which would be otherwise invisible to the naked eye, suddenly become visible in the resultant image.

It is another object of the invention to provide a technique which removes the distraction of motion artifacts. Accordingly, image stabilization is applied to provide a consistent reference for the resultant image, while extraneous motion becomes invisible by the very nature of the usage of multiple image frames.

It is a further object of the invention to reduce the overall radiation dosage to the patient. Accordingly, the acquisition of a multi-purpose image having superior spatial and contrast resolution, from a single fluoroscopic sequence, drastically decreases the overall exposure of the patient.

It is a still further object of the invention to provide a technique which is particularly well suited for mammography. In particular, the elimination of motion artifact by the instant invention means that the mammographic image can be acquired with less painful compression of the breast, and can be more feasibly acquired at mobile screening units. In addition, the instant invention can produce a useful image with less radiation exposure, and will produce a more useable image by virtue of the decreased compression.

It is yet a further object of the invention to provide a technique which is particularly well suited for evaluating trauma patients, the elderly, children, or any patient who has difficulty remaining still during the extended exposure necessary for a radiographic examination. Accordingly, the motion artifact eliminating properties of the present invention allow the acquisition of a useable image even in the case of such patients, and reduces the necessity for increased radiation exposure from image acquisition repetition often necessitated by moving patients.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

The invention is a process for creating a resultant image from a fluoroscopic sequence which comprises a plurality of individual fluoroscopic images. The process comprises major steps of image acquisition, image stabilization, and image combination.

Figure 1:
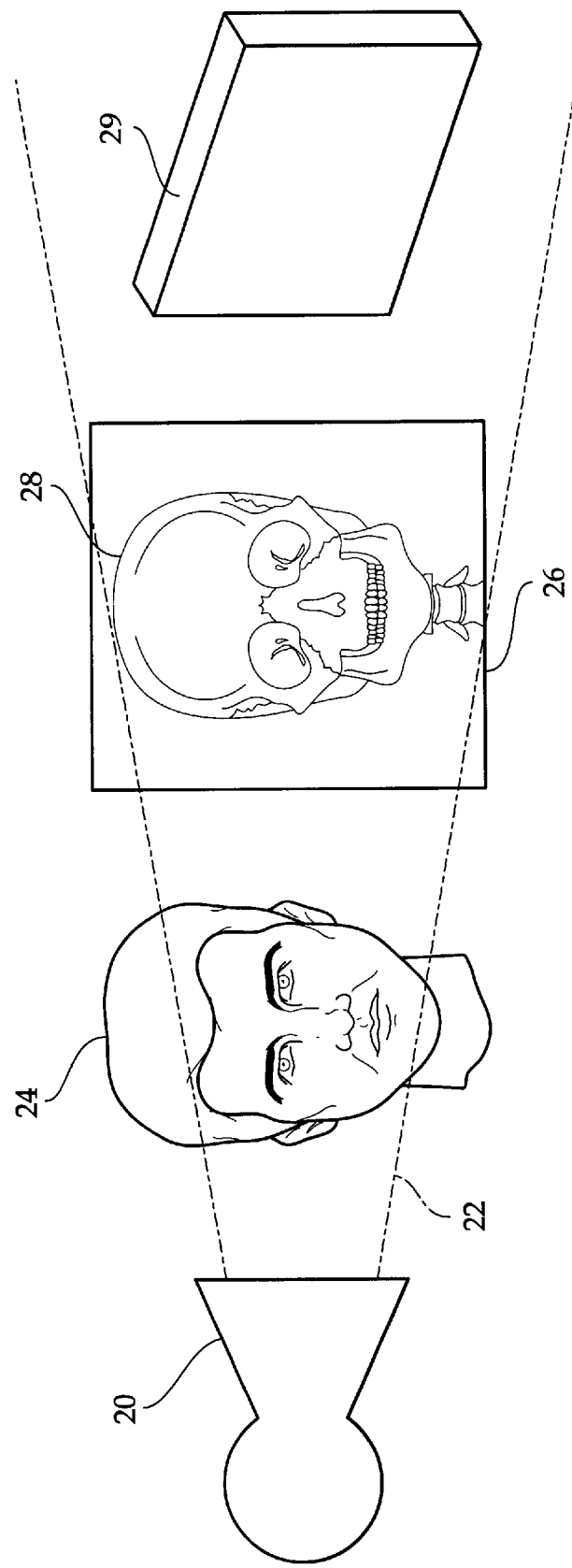
FIG. 1 is a diagrammatic perspective view, illustrating apparatus for acquiring fluoroscopic images for processing according to the present invention.

Image acquisition occurs through conventional fluoroscopic techniques. Referring to FIG. 1, an x-ray source 20 produces a photon ray 22, which is directed at a subject 24. According to various physical properties of the subject 24 which is beyond the scope of the instant discussion, a portion of the photon ray 22 will travel through the subject 24 and strike a fluoroscopic screen 26, producing a fluoroscopic image 28 of visible light which can therefore be observed by the unaided eye. A receptor 29, comprising a moving picture film recorder, a digital video camera, or the like, records the fluoroscopic image 28, and continues to record as the image changes. Over a short time period of time—perhaps one second, the receptor device 29 thus captures a series of perhaps thirty individual images, which is known as a fluoroscopic sequence. In the case of digital imaging, each image is made up of pixels, and has a resolution which is proportional to the number of pixels. Each pixel has a pixel level, wherein the pixel level are quantized at a fixed number of levels, for example 256 levels representing various brightness levels between complete darkness and saturation.

Image stabilization involves positionally stabilizing the subject among the various individual fluoroscopic images. In order to successfully complete image combination, the subject must be in a consistent position throughout all the images. Accordingly an image stabilization technique is performed on the individual fluoroscopic images to produce a series of position stabilized individual images. In the case of digital images, such an image stabilization technique would typically include a pixel shift to align the position of the subject within the various images with any set reference point. The actual stabilization technique used is unimportant to the present invention, since numerous techniques are available to stabilized the subject within a temporal sequence of images. In particular, image stabilization techniques and algorithms developed for handheld "camcorders" is entirely suitable for stabilization required by the present invention. For the purposes of the present invention, the individual images can even be aligned "by hand" using a computer graphics program.

To achieve the best quality resultant image, not all individual images should be used. Accordingly, during image stabilization, some individual images may be discarded. In particularly, images outside the standard deviation when compared to the rest of the images should be discarded, and will not become part of the stabilized individual images.

Image combination involves fractionating the position stabilized individual images to produce fractionated individual images, and summating the fractionated individual images to produce the result image. Fractionating the individual images involves multiplying the individual images by a coefficient equal to the inverse of the number of stabilized individual images. For example if thirty stabilized individual images are employed, the coefficient is 1/30.

Multiplication of the individual images by the coefficient, in the case of digital imaging, actually means multiplying the level of each pixel by the coefficient. However, care should be taken that the multiplication preserves sufficient precision to ensure that information is not lost through quantization. To ensure that information is not lost, each pixel of the fractionated image must have a granularity of the inverse of the coefficient times the granularity of the stabilized individual images. For example if thirty stabilized individual images are stored in an 8-bit configuration, having 256 pixel levels; and fractionating involves multiplying the images by a coefficient of 1/30; then the fractionated individual images must be capable of storing 256 times 30, or 7680 different levels.

Summation involves adding all of the fractionated images, pixel by pixel. It should now be apparent why the image stabilization step is important, since it is highly desirable that pixels representing the same location on the subject should be added to each other. Once all corresponding pixels from all of the fractionated individual images have been added, a resultant image is created.

The resultant image has unexpected sharpness and clarity when compared with any of the individual fluoroscopic images that it was derived from. Unexpectedly, features not visible in any of the fluoroscopic images are suddenly clearly visible in the resultant image. In particular, features not visible because of quantum mottle, or features which show as very subtle variations between light and dark become visible.

Artifacts present in the individual fluoroscopic image have a tendency to disappear in the resultant image. In particular, an artifact which is present in just a few frames will become invisible once fractionated. Even a large object moving across the x-ray field during the fluoroscopic sequence will disappear in the resultant image, because its visibility "strength" is drastically diminished during fractionation.

Figure 2:
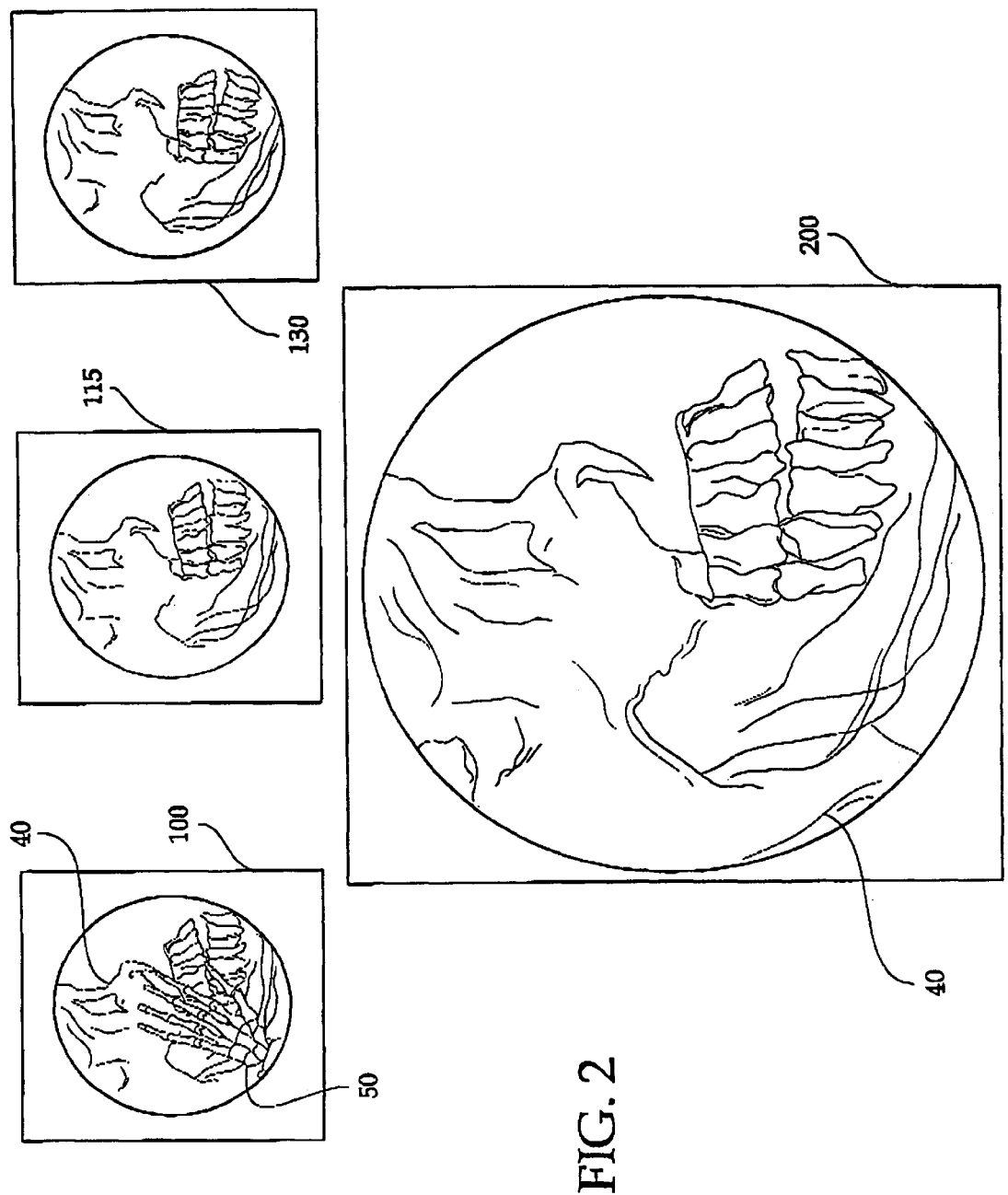
FIG. 2 is a diagrammatic view, illustrating three sample frames from a fluoroscopic sequence, and a resultant image, illustrating a skull and hand in motion, wherein the skull is deemed the subject, and the hand is deemed an artifact.

Referring to FIG. 2, an example is provided showing three images from a fluoroscopic sequence 100, 115, and 130, as well as a resultant image 200. In the images, a skull 40, and a hand 50 is illustrated. Throughout the frames of this fluoroscopic sequence, both the skull 40 and the hand 50 are in motion, moving independently of each other. However, the during image stabilization, the skull 40 is deemed to subject, and the hand 50 is an artifact. According, in the stabilized individual images, the skull 40 has a consistent position, whereas the hand 50 has an arbitrary position. Because the skull has a consistent position, its presence in the resultant image 200 is strong. However, because the hand is in motion, once fractionated it becomes virtually invisible in the resultant image 200. Accordingly, the undesirable artifact of the hand 50 is eliminated in the resultant image 200 by the present invention.

Using the process as outlined above to form the groundwork, additional features, steps, and enhancements can be applied with a resulting increase of the usefulness of the system of the present invention. For example, multiple kV values can be used to create composite images, stereoscopic imaging principles can be applied using the present invention, and mammography can be made less painful and more accessible with less radiation exposure.

Because different tissue responds differently to x-rays having different kV values, using the present invention with a pulsed x-ray, different fluoroscopic images in the same fluoroscopic sequence can be acquired wherein the underlying x-rays were created with differing kV values. However, when the images are fractionated and then summated, a composite image is created having features which would not otherwise simultaneously appear on a single x-ray image. As a result, the patient is spared the increased radiation exposure which would otherwise be required to obtain multiple radiographic x-rays.

With regard to mammography, the present invention allows mammography to be performed using conventional fluoroscopic apparatus. Because of the inherent image stabilization performed in creating the resultant image, a diagnostic quality mammographic image can be created without severely compressing the breast. Also, because motion artifacts are largely eliminated by the process, mobile mammography centers can provide more effective diagnosis. In other embodiments or variations of the invention, different techniques and devices such as cardiac gating, image intensifiers, varying kV, may be utilized to achieve further diagnostic benefits.

In conclusion, herein is presented a system for providing diagnostic quality x-ray images from a series of individual fluoroscopic images. The resulting image has superior quality compared to any of the individual fluoroscopic images—which has several implications for the usefulness of fluoroscopy for a variety of diagnostic purposes for which it had previously not been suitable.

What is claimed is:

1. A process for producing a diagnostic quality x-ray image from a fluoroscopic sequence, comprising:

acquiring a plurality of individual fluoroscopic images;

stabilizing the individual fluoroscopic images to create stabilized individual images in which the subject is in a consistent position within said stabilized individual images; and fractionating the stabilized individual images to create fractionated individual images;

summating the fractionated individual images to create the resultant image.

2. The process for producing a diagnostic quality x-ray image as recited in claim 1, wherein each individual fluoroscopic image comprises a plurality of pixels, each pixel having a pixel level, and wherein the step of fractionating the stabilized individual images further comprises multiplying each pixel level by a coefficient equal to the inverse of the number of stabilized individual images.

3. A process for producing a diagnostic quality x-ray image, wherein not all individual fluoroscopic images become stabilized individual images wherein fluoroscopic images which are outside the standard deviation of the entire fluoroscopic sequence are discarded.

4. The process for producing a diagnostic quality x-ray image as recited in claim 3, wherein each individual fluoroscopic image is acquired with a certain kV value, and wherein some of the individual fluoroscopic images in the fluoroscopic sequence have different kV values than other individual fluoroscopic images in the same fluoroscopic sequence.

* * * * *